United States Patent [19]

Lee et al.

[11] Patent Number: 5,792,412
[45] Date of Patent: Aug. 11, 1998

[54] APERTURED FILMS HAVING DURABLE WETTABILITY AND PROCESSES FOR MAKING THEM

[75] Inventors: Yann-Per Lee, Fairfield, Ohio; Ronald Bernz Holzwarth, Backnang, Germany; Lanying Wu, West Chester, Ohio

[73] Assignee: The Procter & Gamble Company, Cincinnati, Ohio

[21] Appl. No.: 713,377

[22] Filed: Sep. 13, 1996

[51] Int. Cl.$^6$ ................................ B29D 27/00
[52] U.S. Cl. ................ 264/504; 264/154; 264/156; 264/210.6; 264/300; 264/570; 264/DIG. 62; 264/DIG. 70; 428/131; 428/304.4
[58] Field of Search ............... 264/504, 154, 264/156, 300, 210.6, DIG. 62, DIG. 70

[56] References Cited

U.S. PATENT DOCUMENTS

| | | | |
|---|---|---|---|
| 3,973,068 | 8/1976 | Weber | 428/198 |
| 4,070,218 | 1/1978 | Weber | 156/167 |
| 4,456,570 | 6/1984 | Thomas et al. | 264/22 |
| 4,535,020 | 8/1985 | Thomas et al. | 428/131 |
| 4,535,113 | 8/1985 | Foster et al. | 524/262 |
| 4,609,518 | 9/1986 | Curro et al. | 264/504 |
| 4,629,643 | 12/1986 | Curro et al. | 428/131 |
| 4,637,819 | 1/1987 | Ouellette et al. | 604/369 |
| 4,695,422 | 9/1987 | Curro et al. | 264/504 |
| 4,698,388 | 10/1987 | Ohmura et al. | 525/88 |
| 4,808,178 | 2/1989 | Aziz et al. | 604/385.2 |
| 4,857,251 | 8/1989 | Nohr et al. | 264/103 |
| 4,920,168 | 4/1990 | Nohr et al. | 524/188 |
| 4,923,914 | 5/1990 | Nohr et al. | 524/99 |
| 5,057,262 | 10/1991 | Nohr et al. | 264/211 |
| 5,114,646 | 5/1992 | Nohr et al. | 264/103 |
| 5,120,888 | 6/1992 | Nohr et al. | 524/99 |
| 5,283,023 | 2/1994 | Nohr et al. | 264/103 |
| 5,368,910 | 11/1994 | Langdon | 428/137 |
| 5,413,655 | 5/1995 | Nohr et al. | 156/167 |
| 5,520,875 | 5/1996 | Wnuk et al. | 264/504 |

FOREIGN PATENT DOCUMENTS

| | | | |
|---|---|---|---|
| WO 93/09741 | 5/1993 | WIPO | A61F 13/15 |
| WO 94/28846 | 12/1994 | WIPO | A61F 13/15 |

*Primary Examiner*—Morton Foelak
*Attorney, Agent, or Firm*—Carl J. Roof; E. Kelly Linman; Jacobus C. Rasser

[57] ABSTRACT

This invention relates to a process for forming a single-layer, durably wettable polymeric web having a plurality of apertures. This process comprises melting a mixture of at least one thermoplastic polymer and at least one migratable surfactant and extruding the mixture to form a single-layer, substantially continuous polymeric film. The film is then apertured using high pressure fluid flows. Aperture formation is conducted when the single-layer polymeric film has a contact angle of at least about 30°, to minimize wash-off of the surfactant impregnated in the polymer web. The invention also relates to durably-wettable apertured webs.

25 Claims, 2 Drawing Sheets

APERTURED FILMS HAVING DURABLE WETTABILITY AND PROCESSES FOR MAKING THEM

TECHNICAL FIELD

The present invention relates to a process for making durably wettable, apertured polymeric films that are particularly suitable as topsheets for absorbent articles. In particular, the invention relates to a process for perforating a substantially continuous polymeric film so as to coincide with the pattern of one or more three-dimensional forming structures. This process results in a three-dimensional apertured polymeric web. As described in detail below, the continuous polymeric film is prepared by extrusion of a mixture of polymeric resin and a wetting agent (eg., a surfactant) that is incompatible with the polymeric material. After perforating this film, the incompatible wetting agent migrates or "blooms" to the surface to provide a durably wettable, three-dimensional apertured polymeric web.

The present invention further relates to a durably wettable, apertured plastic web exhibiting highly desirable vapor and durable fluid transmission capabilities, in addition to visual and tactile impressions which are desired to consumers. In another aspect, the present invention relates to a multi-phase process for making such apertured plastic webs.

BACKGROUND OF THE INVENTION

Macroscopically expanded, three-dimensional, apertured polymeric webs are generally known in the art. As utilized herein, the term "macroscopically expanded", when used to describe three-dimensional plastic webs, ribbons and films, refers to webs, ribbons and films which have been caused to conform to the surface of a three-dimensional forming structure so that both surfaces thereof exhibit the three-dimensional pattern of the forming structure, the pattern being readily visible to the naked eye when the perpendicular distance between the viewer's eye and the plane of the web is about 12 inches. By way of contrast, the term "planar", when utilized herein to describe plastic webs, ribbons and films, refers to the overall condition of the web, ribbon or film when viewed by the naked eye on a macroscopic scale. In this context "planar" webs, ribbons and films may include webs, ribbons and films having fine-scale surface aberrations on one or both sides, the surface aberrations not being readily visible to the naked eye when the perpendicular distance between the viewer's eye and the plane of the web is about 12 inches or greater.

One macroscopically expanded, three-dimensional apertured polymeric web which is particularly well suited to transferring fluid deposited on one surface thereof to its opposite surface and thereafter isolating the transferred fluid from a wearer's skin is disclosed in commonly assigned U.S. Pat. No. 3,929,135 issued to Thompson on Dec. 30, 1975, the disclosure of which is incorporated by reference herein. Thompson describes a macroscopically expanded, three dimensional web ( e.g., a topsheet) comprised of liquid impermeable material, but provided with a pattern of tapered capillaries, the capillaries having a base opening in the plane of the topsheet and an apex opening remote from the plane of the topsheet, the apex opening being in intimate contact with the absorbent pad utilized in the disposable absorbent bandage. The Thompson topsheet allows the free transfer of fluids from the wearer's body into the absorbent element of the device while inhibiting the reverse flow of these fluids. This provides a relatively much drier surface in contact with the user than had previously been obtainable.

Another macroscopically expanded, three-dimensional apertured plastic web well suited for use as a topsheet on absorbent bandages such as sanitary napkins is disclosed in commonly assigned U.S. Pat. No. 4,342,314 issued to Radel and Thompson on Aug. 3, 1982, the patent being hereby incorporated by reference herein. The macroscopically expanded, three-dimensional plastic web disclosed in the Radel and Thompson patent exhibits a fiber-like appearance and tactile impression which has been favorably received by consumers when used as a wearer contacting surface.

According to the teachings of the aforementioned commonly assigned patents to Thompson and to Radel, et al., plastic webs of the aforementioned type can be made by applying a fluid pressure differential to the web while it is supported on a three-dimensional forming structure until the web is macroscopically expanded to comply with the three-dimensional cross-section of the forming structure on which it is supported. When aperturing of the macroscopically expanded, three-dimensional web is desired, the fluid pressure differential is applied continuously until such time as aperturing of the web in areas coinciding with the apertures in the forming structure has been completed.

While single-phase (i.e., one aperturing phase) forming processes (including the fluid-based systems discussed above and the vacuum-based systems discussed below) have been successfully utilized in producing macroscopically expanded, three-dimensional apertured plastic webs exhibiting many characteristics generally viewed as favorable by consumers, such single-phase processing techniques are unable to deliver certain desired characteristics in a single finished web structure, particularly at high production speeds.

In this regard, a multi-phase, fluid-based process such as that described in U.S. Pat. No. 4,609,518, issued Sep. 2, 1986 to Curro et al. (hereafter referred to as "'518 patent"), was developed to provide a film with very small and very large apertures immediately adjacent one another. As the patent discloses, the formation of the very small (including micro-sized) apertures in the direction opposite those formed for large apertures hinders the ability of initially unabsorbed fluid from running off the web's surface. Thus, fluid not immediately transported through the large apertures is restrained from running off the web's surface, and is subsequently taken up through the larger apertures and is deposited in the article's core where the web is used as a topsheet material. These outwardly formed small apertures also reduce the level of web/skin contact and reduce the rigidity of the film, and thereby feel more comfortable to the user. Alternatively, the '518 patent discloses films where the very small apertures are formed in the same direction as the macro-apertures.

An alternative to forming apertured, three-dimensional films via use of fluid pressure differentials is the use of vacuum-forming such structures. For example, U.S. Pat. No. 3,054,148 issued Sep. 18, 1961 to Zinunerli describes a perforated film material formed by heating a film on a perforated screen while applying sufficient vacuum to the underside of the screen to form apertures in the film. The use of vacuum formation is limited in that formation of apertures in two directions, such as is described in the '518 patent, is not possible because heating the apertured film for the requisite second pass damages the apertures formed in the first pass. As such, the tactile/feel benefits obtainable using that process are not obtainable using vacuum perforation methods. In addition, micro-sized apertures obtainable using fluid formation (e.g., the '518 patent) is generally not obtainable using vacuum forming processes because typical vacuum power applied in such processes is insufficient to rupture the film to form microsized apertures.

Regardless of the means employed for aperture formation, where a wettable film material is desired, the above references generally obtain such a structure by surface treating the naturally hydrophobic polymeric web with a wetting agent. Surface treatment is generally accomplished by either spraying surfactant onto the web's surface or by dipping the web in a surfactant-containing bath. Regardless of which of these methods is employed, surface treatment suffers from the inability to precisely control the location and level of treatment, as well as adverse effects caused by migration of insignificant amounts of surfactant into apertures and other components (e.g., absorbent core) when the apertured film is used as a topsheet in an absorbent article. Surface treatment further suffers from the disadvantage that desirable wetting agents, or surfactants, tend to be washed off upon repeated exposure to such fluids. Thus, when used as a topsheet in an absorbent article, the treated films lose their ability to transport fluid away from the skin and into the article's core after repeated wettings.

U.S. Pat. No. 4,535,020, issued to Thomas et al. on Aug. 13, 1985, addressed some of the problems associated with surface treating vacuum-formed apertured films by incorporating hydrophilic surfactant in the polymeric resin before extrusion for film formation. After extrusion of the resin/surfactant mixture, and subsequent vacuum formation of the apertures, the incompatible surfactant eventually blooms to the film's surface to provide a more durably wettable web. As indicated above, however, the use of vacuum formation means for aperturing films has inherent limitations relative to the use of fluid formation means.

In this regard, co-assigned U.S. Pat. No. 5,520,875, issued May 28, 1996 to A. J. Wnuk et al., addresses the problem of surfactant wash-off where apertures are formed using a fluid-pressure differential by co-extruding multiple polymeric film layers, referred to therein as core layers and outer layers. The outer layer, which is exposed to the aperture-forming fluid, is free of surfactant, while the core layer contains a migratable surfactant. After co-extrusion and aperture formation, the surfactant migrates from the core layer to the outer layer's surface, to provide a durably wettable multilayer web. As such, the patent addresses many of the undesired aspects of prior aperturing processes. However, this process is clearly limited to the production of multilayer films. Thus, the patent describes a process that requires additional raw materials that may serve no function other than avoiding surfactant wash-off during manufacture, thereby potentially adding unwanted caliper, complexity and/or cost when the laminate is used as an absorbent article topsheet. Similarly, the patent requires co-extrusion of separate layers of material, which may add complexity to the formation process and formation equipment.

In spite of the teachings of the prior art there remains a need for a single-layer, apertured film material that offers both durable wettability and a soft feel to the skin. There also remains the need for a process that provides a single-layer, apertured film having improved durable wettability, wherein the process minimizes wash-off of surfactant during aperture formation using a fluid pressure differential. There also remains the need for a multi-phase process for producing a single-layer, apertured film having improved durable wettability and soft feel to the skin.

Accordingly, it is an object of the present invention to provide a process wherein various combinations of previously incompatible characteristics can be provided in a single-layer, apertured polymeric web.

It is another object of the present invention to provide a multi-phase process for producing durably wettable, apertured plastic webs wherein the different phases of the process may be separated from one another either temporally or spatially or both.

It is still another object of the present invention to provide apertured plastic webs which offer improved durable wettability along with highly preferred appearance, softness and tactile impression.

It is still another object of the present invention to provide a process for fluid aperturing a continuous polymeric film wherein the process minimizes surfactant wash-off. Minimizing surfactant wash-off provides two distinct benefits. First, reduced levels of surfactant are required to obtain a wettable web. Second, reducing the level of washed-off surfactant during film processing prevents undesired foaming and alleviates the adverse effect surfactants have on machine performance after continuous exposure.

SUMMARY OF THE INVENTION

The present invention relates to a continuous process for forming a single-layer, durably wettable polymeric web having a plurality of apertures. This process comprising the steps of:

(a) melting a mixture of at least one thermoplastic polymer and at least one migratable surfactant and extruding the mixture to form a single-layer, substantially continuous polymeric film;

(b) continuously supporting the film on a forming structure exhibiting a three-dimensional pattern defined by a multiplicity of apertures which place the opposed surface of the forming structure in fluid communication with one another, the forming structure moving in a direction parallel to the direction of travel of the web of film and carrying the film in the direction; and (c) applying a fluid pressure differential across the thickness of the film along the direction of movement of the forming structure exhibiting the apertures, the fluid pressure differential being sufficiently great to cause the film to rupture in those areas coinciding with the apertures in the forming structure;

wherein aperture formation in Step (c) is performed when the surface of the film formed in Step (a) has a contact angle for water of at least about 30°.

When this single-phase process is employed, the apertures in the forming structure may be either macroscopic, microscopic, or both macroscopic and microscopic in size. Films prepared using this process have the apertures formed in only one direction.

The invention further pertains to a multi-phase process for forming a single-layer, durably wettable polymeric web having apertures formed in both directions. The process comprises the steps of:

(a) melting a mixture of at least one thermoplastic polymer and at least one migratable surfactant and extruding the mixture to form a substantially continuous polymeric film;

(b) continuously supporting the film on a first forming structure exhibiting a multiplicity of apertures (preferably the apertures are microscopic in size) which place the opposed surfaces of the forming structure in fluid communication with one another, the forming structure moving in a direction parallel to the direction of travel of the film and carrying the film in the direction;

(c) applying a first fluid pressure differential across the thickness of the film along the direction of movement of the forming structure exhibiting the apertures, the fluid pressure differential being sufficiently great to cause the film to rupture in those areas coinciding with the apertures in the forming structure;

(d) continuously supporting the apertured web on a second forming structure exhibiting a multiplicity of apertures (preferably, the apertures are macroscopic in size when the apertures in the first forming structure are microscopic in size) which place the opposed surfaces of the second forming structure in fluid communication with one another, the second forming structure moving in a direction parallel to the direction of travel of the apertured web and carrying the apertured web in the direction; and (e) applying a second fluid pressure differential across the thickness of the apertured web along the direction of movement of the forming structure, wherein the second fluid pressure differential is sufficiently great to rupture the apertured web in those areas coinciding with the apertures in the second forming structure, while substantially maintaining the integrity of the apertures formed by the first fluid pressure differential;

wherein aperture formation in Step (c) is performed when the film formed in Step (a) has a contact angle for water of at least about 30°, and wherein aperture formation in Step (e) is performed when the surface of the apertured web formed in Step (c) that will be subjected to the second fluid pressure differential in the second forming structure has a contact angle for water of at least about 30°.

As indicated above, it is preferred that one of the forming structures in the multiphase process will have microscopic-sized apertures, and the other forming structure will have macroscopic-sized apertures. Most preferably, the first forming structure will have microscopic-sized apertures and the second forming structure will have macroscopic-sized apertures. Further, unlike the single-phase process, the multiphase process allows for aperture formation in two different directions. That is, after the continuous web is apertured on the first forming structure, the apertured web may be introduced to the second forming structure such that the apertures are formed in a direction opposite those formed on the first forming structure. This is accomplished by simply introducing the apertured web such that the surface contacting the second forming structure was not the surface in contact with the first forming structure. It is apparent that the multi-phase process of the present invention may be carried out to obtain webs having micro-sized holes in both direction or macro-sized holes in both directions.

The invention further pertains to a single-layer, fluid-handling polymeric web comprising a thermoplastic material and a migrating surfactant, the web having first and second surfaces, the web further comprising a multiplicity of microscopic apertures originating in the first surface of the web, the microscopic apertures exhibiting a degree of capillary suction sufficient to transmit static fluid contained on the surface of objects which contact the first surface of the web generally in the direction of the second surface of the web by capillary attraction.

In a preferred embodiment, the single-layer web containing the thermoplastic and the migratable surfactant comprises:

a. a multiplicity of apertures of macroscopic cross-section for transmitting fluids which are dynamically deposited on the first surface of the web to the second surface of the web using the dynamic and gravitational head of the fluid as a primary driving force, each of the macroscopic apertures originating in the first surface of the web and having a continuously interconnected sidewall extending in the direction of the second surface of the web, the continuously interconnected sidewall terminating to form at least one aperture in the second surface of the web, whereby the bulk of the dynamically deposited fluid is transmitted from the first surface to the second surface of the web by the macroscopic apertures; and b. a multiplicity of microscopic apertures originating in either the first or the second surface of the web, the microscopic apertures exhibiting a degree of capillary suction sufficient to transmit static fluid contained on the first surface of objects which contact the first surface of the web generally in the direction of the second surface of the web by capillary attraction.

While the present invention may take many different executional forms, the web forming processes of the invention comprise at least one aperture-forming phase which utilizes a fluid pressure differential to achieve its objective. Where a durably wettable web having only macro-sized or micro-sized apertures is desired, only one aperture forming phase is required. In contrast, where a durably wettable web having both macro-sized and microsized holes is desired, two discrete forming phases, each of which utilizes a fluid pressure differential, are employed. One of the phases involves microscopic aperturing of the web in those areas coinciding with the microscopic apertures in the one forming structure, using sufficient fluid pressure differentials. The other phase involves macroscopic aperturing of the web in those areas coinciding with the macroscopic apertures in another forming structure using sufficient fluid pressure differentials.

Applicants have discovered that regardless of whether a single-layer polymeric web having only macro-sized or macro-sized holes, or a single-layer polymeric web having both macro- and micro-sized holes, is desired, obtaining durable wettability utilizing an impregnated, migratable surfactant requires that aperture formation be concluded within specific time periods. In particular, as is described in detail below, it is important that aperture formation (macro and/or micro) be concluded before a significant portion of the surfactant has "bloomed" to the polymeric web's surface. Aperture formation prior to significant blooming minimizes surfactant wash-off that would otherwise result from the high-pressure fluid differentials applied to the planar film. This provides benefits in that less surfactant is required in the resin/surfactant mix to obtain desired wettability of the resulting film. In addition, minimizing surfactant wash-off during processing reduces undesirable foaming (and the corresponding use of anti-foaming agents), reduces the adverse effects caused by prolonged equipment exposure to high levels of surfactant contained in water systems, reduces undesired environmental discharge concerns, and minimizes undesired re-deposition of surfactant on the apertured web.

The order in which the aperture forming phases are applied will depend upon the particular characteristics desired in the resultant three dimensional, apertured polymeric web. Where at least two forming phases are necessary, they may be performed on a single forming structure including all of the features desired in the resultant web or on multiple forming structures, each of which imparts only a portion of the desired features to the web. The fluid media applied during each of the forming phases may be similar or dissimilar to one another, again depending upon the particular characteristics desired in the resultant polymeric web.

DETAILED DESCRIPTION OF THE PRESENT INVENTION

Figure 1:
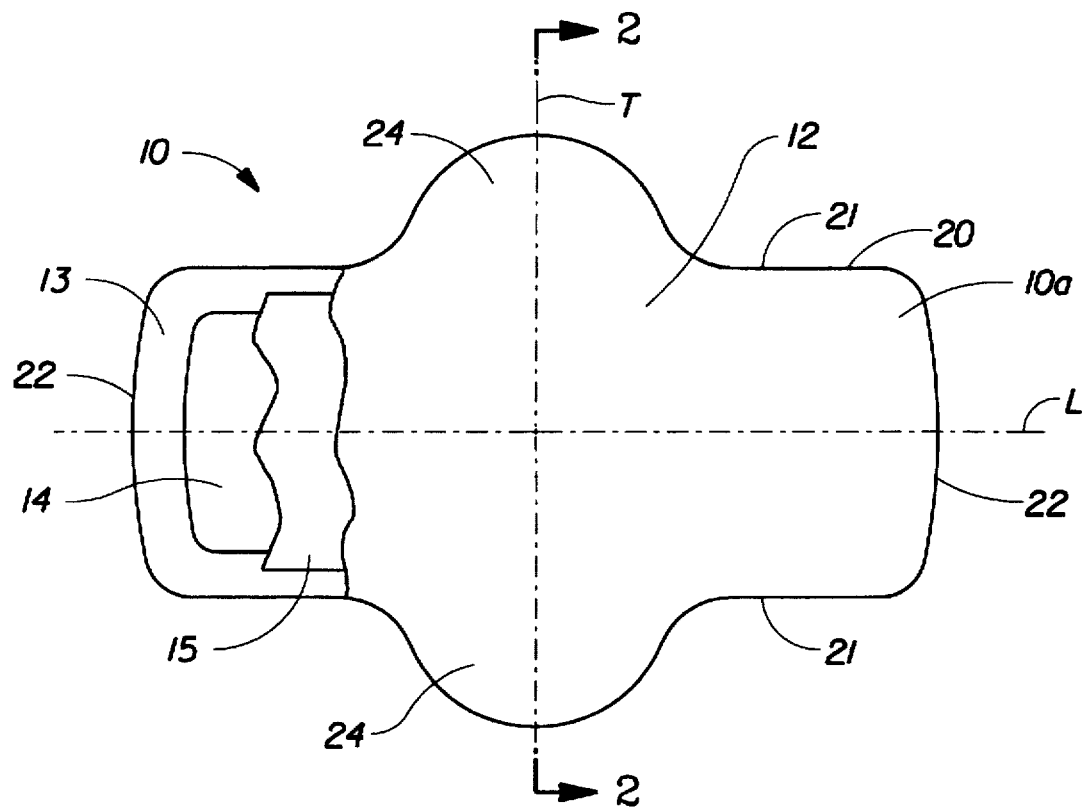
FIG. 1 is a top plan view of a sanitary napkin with portions of the sanitary napkin cut away to more clearly show the construction of the sanitary napkin.

While the present invention will be described in the context of providing durably wettable, single-layer apertured webs particularly suited for use as a wearer contacting surface on absorbent articles such as sanitary napkins, disposable diapers, wound dressings and the like, the present invention is in no way limited to such applications. To the contrary, the present invention may be practiced whenever it is desired to produce plastic films or webs exhibiting properties, characteristics, aesthetics, etc. not previously obtainable using prior art web forming processes. The apertured patterns created may be of any desired shape, they may be regulated or random, reticulated or non-reticulated, continuous or interrupted, or any desired combination thereof. Furthermore, while the webs formed by the processes of the present invention are single-layer films, they may be combined after formation with other materials to form a laminated structure. Similarly, the single layer films may be further processed to modify the surface characteristics of one or both surfaces of the apertured film. For example, in one embodiment, a film of the present invention can be surface-treated with a hydrophobic material in accordance with the teachings of co-pending, co-assigned U.S. patent application Ser. No. 08/442,935, filed May 31, 1995 by Ouellette et al., to provide a material that exhibits a surface energy gradient. In a preferred embodiment for obtaining a material with such a gradient, the apertured film of the present invention is a web having macro-size apertures formed in one direction and micro-size apertures formed in the opposite direction. It is further preferred that the web be subjected to corona discharge treatment (discussed below) at some time prior to treating the web with the hydrophobic material, to enhance the bonding of the hydrophobic material to the web.

The detailed description of the structures disclosed herein and their suggested use as topsheets and/or backsheets in a disposable absorbent articles context will allow one skilled in the art to readily adapt the invention to produce webs well suited to other applications.

I. Definitions

With regard to the apertured webs of the present invention, a given aperture's "amplitude" refers to the distance from the surface where the aperture originates to the surface where the aperture terminates.

As used herein, the term "female side" means the side or surface of a web where the apertures being described originate. In contrast, the term "male side" means the side or surface of a web where the apertures being described terminate. As such, during a given phase of aperture formation, the surface of the web being contacted by fluid pressure will be the female side with respect that aperture formation phase, while the side in contact with the forming structure (and not exposed to fluid pressure) is the male side with respect to that aperture formation phase. Of course, for webs having apertures formed in opposite directions, both surfaces will have female apertures and male apertures.

As used herein, the terms "microscopic" and "microsized" are used interchangeably and refer to web apertures (and apertures in a forming structure for forming such web apertures) that are not individually identifiable when observed by the naked eye when the perpendicular distance between the viewer's eye and the plane of the web is about 12 inches. In contrast, the terms "macroscopic" and "macrosized" are used interchangeably and refer to web apertures (and apertures in a forming structure for forming such apertures) that are individually identifiable when observed by the normal naked eye when the perpendicular distance between the viewer's eye and the plane of the web is about 12 inches. Typically, use of the term "microscopic" refers to an aperture having as its largest dimension, as measured perpendicular to its amplitude and on the female side of the web, a distance of not more than about 300 µm, preferably not more than about 250 µm, more preferably not more than about 200 µm, still more preferably not more than about 150 µm; while "macroscopic" refers to an aperture having a dimension of greater than about 300 µm, as measured perpendicular to its amplitude and on the female side of the web.

As used herein, the term "migratable surfactant" refers to any surfactant that is chemically incompatible with the thermoplastic polymer with which it is combined, such that it will migrate to the film's surface over time to alter the fluid handling dynamics of the polymer's surface. Representative materials useful as the surfactant and the thermoplastic polymer are described below.

II. Forming Polymeric Webs Suitable for Aperturing

Preferred polymeric materials useful herein include polyolefins, particularly polyethylene, polypropylene and copolymers having at least one olefinic constituent. Other thermoplastic materials such as polyesters, nylons, copolymers thereof and combinations of any of the foregoing may also be suitable as the polymeric material.

The surfactant materials useful herein are necessarily incompatible with the polymeric material, such that they will migrate to the film's surface after aperture formation. Polymeric webs having migratable surfactants provide durable wettability primarily because when surfactant molecules are washed off during exposure to fluids in use, they are replaced by additional molecules contained within the polymeric web. (The criticality of when aperture formation is conducted relative to the blooming of surfactant to the film's surface is discussed in detail below.) In addition, the surfactant must be such that it renders the resulting film relatively hydrophilic.

In general, surfactant molecules are composed of functional groups having opposing solubility tendencies. Typically one group is a non-polar/oil-soluble/water-insoluble/hydrophobic (e.g., hydrocarbon, silicone) chain and the opposing group is a polar/water-soluble/hydrophilic group. Surfactants are classified according to the electrical charge of the polar hydrophilic moiety. In anionic surfactants the polar group carries a negative charge. In cationic surfactants the polar group carries a positive charge. In amphoteric surfactants both positive and negative charges are present in the same molecule. In non-ionic surfactants, there is no electrical charge on the molecule. For example, the polar hydrophilic group in non-ionic surfactants can be a chain of water-soluble ethylene oxide units or a group bearing multiple hydroxyl functionalities, for example groups derived from glycerol or sorbitol. The chemistry of surfactants is very broad and is described more fully in the Kirk-Othmer Encyclopedia of Chemical Technology, 3rd Edition, Volume 22, pp. 332–432, herein incorporated by reference.

In the process of the present invention, surfactants from each class mentioned above can be used. However, where the resulting three dimensional, apertured plastic web is to be used in absorbent articles such as sanitary napkins, pantiliners, disposable diapers, incontinent articles, and the like, where contact with human skin tissue is expected, the skin irritation potential of the surfactant must be considered. In general, cationic surfactants tend to be more irritating than anionic, which tend to be more irritating than either amphoteric or non-ionic types. Thus, particularly preferred surfactants are those of non-ionic families, including, for example: sorbitan esters, ethoxylated sorbitan esters, silicone copolymers, fluorochemcial-based surfactants, alcohol ethoxylates, alkylphenol ethoxylates, carboxylic acid esters, glycerol esters, polyoxyethylene esters of fatty acids, polyoxyethylene esters of aliphatic carboxylic acids related to abietic acid, anhydrosorbitol esters, ethoxylated anhydrosorbitol esters, ethoxylated natural fats, oils, and waxes, glycol esters of fatty acids, carboxylic amides, diethanolanine condensates, monoalkanolamine condensates, polyoxyethylene fatty acid amides, polyalkyleneoxide block copolymers. Preferred non-ionic surfactants include sorbitan esters, silicone copolymers and fluorochemcial-based surfactants. Particularly preferred surfactants useful herein include Atmer 100° (sorbitan-based; ICI), Atmer 645° (ICI), Q4-3667 (silicone copolymer; Dow Corning), and FC1802 (fluorochemical; 3M Company). The skilled artisan will recognize that any surfactant that is incompatible with the polymeric component and is capable of modifying the surface characteristics of the polymer may be used in the practice of the present invention.

The average molecular weight of surfactants selected for the present invention may range from about 200 grams per mole to greater than 50,000 grams per mole. Preferred surfactants have an average molecular weight of from about 300 to about 50,000 grams per mole.

The surfactant level initially blended with the polymeric resin before film formation can be as much as 10 percent by weight of the total resin/surfactant mixture. Surfactants in the preferred average molecular weight range (300–50,000 grams/mole) can be added at lower levels, generally at or below about 5 weight percent of the total film structure.

The polymeric film that is formed prior to aperturing may be processed using conventional procedures for producing films on conventional extruded film-making equipment. Pellets of the above described components (including surfactant and one or more polymers in the form of pellets) can be first dry blended and then melt mixed in the extruder. Alternatively, if insufficient mixing occurs in the extruder, the pellets and surfactant can be first dry blended and then melt mixed in a precompounding extruder followed by repelletization prior to film extrusion.

In general, polymers can be melt processed into films using either cast or blown film extrusion methods both of which are described in "Plastics Extrusion Technology"— 2nd Ed., by Allan A. Griff (Van Nostrand Reinhold—1976), herein incorporated by reference. Cast film is extruded through a linear slot die. Generally, the flat web is cooled on a large moving polished metal roll. It quickly cools, and peels off the first roll, passes over one or more auxiliary rolls, then through a set of rubber-coated pull or "haul-off" rolls, and finally to a winder.

In blown film extrusion, the melt is extruded upward through a thin annular die opening. This process is also referred to as tubular film extrusion. Air is introduced through the center of the die to inflate the tube and causes it to expand. A moving bubble is thus formed which is held at constant size by control of internal air pressure. The tube of film is cooled by air blown through one or more chill rings surrounding the tube. The tube is next collapsed by drawing it into a flattening frame through a pair of pull rolls and into a winder.

III. Forming Durably Wettable, Apertured Polymeric Webs

The processes of the present invention provide durably wettable, single layer webs preferably having either macro-sized or micro-sized apertures, or both macro-sized and micro-sized apertures. Regardless of the desired end product, Applicants have discovered that to minimize wash-off of the migratable surfactant during hydroformation, aperturing must be accomplished prior to migration of a significant portion of surf cat to the polymeric film's surface.

For a given polymer/surfactant combination, the rate at which the surfactant will migrate to the polymeric film's surface (and thereby reduce the contact angle for water) is a function of several factors, including the thickness of the film, the nature of the surfactant (such as molecular size, polarity, compatibility with the polymer resin, molecular weight, chemical structure, etc.), the concentration of surfactant in the polymer, the temperature at which the surfactant-impregnated polymer is stored after extrusion, extrusion conditions (e.g., extrusion temperature) and the nature of the polymer resin matrix (e.g., crystallinity).

For a given surfactant/polymer mixture, the rate of surfactant migration to the film's surface will generally increase with increasing temperature and decreases with decreasing temperature. The skilled artisan will recognize that routine experimentation, using the methods described in the Test Methods section, will allow determination of when aperturing must be accomplished for a given surfactant/polymer combination that is to be processed to accomplish aperturing when the material's contact angle for water is at least about 30°. As discussed in detail herein, the criticality is that with regard to processing films having either micro- or macro-sized holes, aperturing must be performed at a time when the unapertured film (containing polymer and surfactant) has a contact angle for water of at least about 30°, preferably at least about 40°, more preferably at least about 50°. With regard to films having both macro- and micro-apertures, hydroformation of the first set of apertures must be formed when the essentially continuous film has a contact angle for water of at least about 30°, preferably at least about 40°, more preferably at least about 50°; and final aperturing— micro or macro—must be performed when the macro or micro apertured film, has a contact angle for water of at least about 30°, preferably at least about 40°, more preferably at least about 50°. (As indicated above, the timing of the second phase of aperture formation is determined by measuring the contact angle of the surface that will be exposed to fluid pressure differential during the next (second) phase of aperture formation. It is this surface that is contacted by high fluid pressures and is subject to surfactant wash-off.)

Known methods for aperture formation using fluid pressure differential are useful herein, so long as aperturing is conducted within the period after film extrusion found to be critical by Applicants. Preferred, non-limiting embodiments are discussed below.

A particularly preferred multi-phase forming process of the present invention is schematically illustrated in FIG. 1 of U.S. Pat. No. 4,609,518, issued Sep. 2, 1986 to Curro et al. (hereafter "'518 patent"), which is incorporated by reference herein. In essence, the forming process illustrated in FIG. 1 of the '518 patent, and further discussed with regard to FIGS. 2–4, can be used in the present invention, so long as aperture formation of unapertured web 10 in forming structure 15 occurs before the unapertured web has a contact angle for water of at least about 30° and final aperture formation in forming structure 50 of the apertured web 10 (according to the present invention, comprising, e.g., a polymeric material such as polyethylene or polypropylene and a migratable surfactant) formed in forming structure 15 is conducted when the surface of the apertured web from forming structure 15 that will not contact forming structure 50 has a contact angle for water of at least about 30°, as measured via the method described in the Test Method section. The formation of the microapertures in the first phase and formation of the macroapertures in the second phase, per the '518 patent is preferred. However, reversing the order of aperture formation is possible and is within the scope of this invention.

Per FIG. 1 of the '518 patent, after completion of the first phase of the web forming process in forming structure 15, the apertured web 10 of polymer/surfactant blend may be fed to the second phase of the forming process for additional aperturing or to a rewind station for temporary storage. In the latter circumstance, application of the second phase of the process may be deferred until a later date, perhaps at a different location. As noted above, however, application of the second phase must be conducted when the web 10 from the first aperturing phase in forming structure 15 exhibits a contact angle for water of at least about 30°.

FIG. 5 of the '518 patent is a simplified illustration of an alternative polymeric web forming process that can be adapted for use in the present invention. Like the process generally illustrated in FIG. 1, the process shown in FIG. 5 is carried out in two discrete phases. As can be seen from a comparison of FIGS. 5A and 5B to FIGS. 1B and 1C, respectively, the first phase of the process which provides the micro-sized apertures 11 in the web of film 10 (containing polymer and migratable surfactant when adopted to the present invention) is essentially identical. However, in the embodiment shown in FIG. 5, the polymer/surfactant film is fed directly onto a second forming structure 50, identical to the one shown in FIG. 1, without reverse wrapping of the film. Accordingly, surface 17 is placed in contact with forming structure 50, while surface 14 is placed so that it will be contacted by the liquid jet 100 issuing from fluid nozzle 90.

With the exception of reversing the position of stationary baffles 70 and 80 and reversing the direction of rotation of forming structure 50 about forming drum 58, the second phase of the process shown in FIG. 5 is substantially identical to that shown in FIG. 1. Again, in adapting the process shown in FIG. 5, macroscopic aperturing in forming structure 50 must occur when the surface of the microapertured web 10 from the first aperturing phase that will not contact forming structure 50 exhibits a contact angle for water of at least about 30°. Reversing the order so as to form the macroapertures first, followed by microaperture formation, is within the scope of the present invention.

Notwithstanding the advantages afforded by the use of multiple forming structures in carrying out the multi-phase web forming process of the present invention, there may be circumstances when it is particularly desirable to practice the present invention using only a single three-dimensional forming structure. These situations may involve the production of polymeric webs wherein it is desired to provide macroscopic expansion to form relatively large apertures in combination with micro-sized aperturing of the web only in the non-debossed land areas of the web, i.e., the sidewalls of the capillary networks would remain substantially imperforate. It may also in certain instances be desirable to provide macroscopic conformance of a plastic web to the three-dimensional patterns of the forming structure with only micro-sized aperturing rather than macro-sized aperturing in the end walls of the capillary networks formed in the web. In still other situations, it may be desirable to provide micro-sized aperturing in the end walls of the capillary networks in conjunction with micro-sized aperturing in the non-debossed land areas of the web without micro-sized aperturing in the sidewalls of the capillary networks. The multi-phase process embodiments illustrated in FIGS. 6, 8, 9 and 10 of the '518 patent are illustrative of multi-phase forming processes of the present invention which are carried out utilizing only a single forming structure containing not only the desired macroscopic cross-sectional profile, but also the desired micro-scale aperturing pattern.

Of course, where durably wettable webs having only macro-sized or micro-sized apertures are desired, the steps described in the '518 patent for micro- or macro aperturing, respectively, may be eliminated. Per the present invention, such aperturing must be completed when the web 10 of polymer/surfactant blend has a contact angle for water of at least 30°. For the production of durably wettable webs having only micro-sized apertures, film formation may alternatively be conducted according to the processes described in U.S. Pat. No. 4,629,643, issued Dec. 16, 1986 to Curro et al. (hereafter "'643 patent"), which is incorporated by reference herein. The webs of the present invention may also be prepared using the processes described generally in U.S. Pat. No. 4,695,422, issued Sep. 22, 1987 to Curro et al., the disclosure of which is incorporated by reference herein. Again, those processes are modified in accordance with the teachings herein with regard to the timing of aperture formation.

Details as to the construction, positioning, etc., of the nozzle for fluid aperturing are fully set forth in the '518, '643 and '422 patents. For purposes of aperturing webs of the type herein described to the, the high pressure liquid jet nozzle is typically operated at a pressure in the range of about 400 psig to about 1200 psig.

The webs of the present invention are optionally subjected to corona discharge treatment at any point in the manufacturing process subsequent polymer/surfactant extrusion to form the continuous, unapertured web. Thus, for example, corona discharge treatment may, when desired, occur prior to aperture formation, after final aperture formation, or between aperture forming phases when more than one phase is employed. The use of corona discharge treatment may provide the webs of the present invention with enhanced durable wettability. Methods for corona discharge treating polymeric films is well known in the art. (See, e.g., "Corona Treatment: An Overview", Markgraf, D. A., TAPPI SEMNAR NOTES—1986 COEXTRUSION, p. 85–91.)

IV. Durably Wettable, Apertured Webs

With the exception of being comprised of polymeric material (e.g., polyolefin) and impregnated surfactant, the preferred apertured webs of the present invention will have structural appearances similar to the webs depicted in the '518, '643 and '422 patents. Webs having only micro-sized apertures may have a structure similar to that depicted as FIG. 1C in the '518 patent. Preferred webs of the present invention have both macroscopic and microscopic apertures, such as the webs depicted in FIGS. 1E, 5D, 6C, 9C and 10C in the '518 patent. Most preferably, the microscopic apertures are formed in a direction opposite the macroscopic apertures, such as is depicted in FIG. 1E of the '518 patent. In a particularly preferred embodiment, the dual-apertured web will have a caliper of about 750 µm.

V. Absorbent Articles

As used herein, the term "absorbent article" refers generally to devices used to absorb and contain body exudates, and more specifically refers to devices which are placed against or in proximity to the body of the wearer to absorb and contain the various exudates discharged from the body. The term "absorbent article" is intended to include diapers, catamenial pads, tampons, sanitary napkins, incontinent pads, training pants and the like, as well as wipes, bandages and wound dressings. The term "disposable" is used herein to describe absorbent articles which are not intended to be laundered or otherwise restored or reused as an absorbent article (i.e., they are intended to be discarded after limited use, and, preferably, to be recycled, composted or otherwise disposed of in an environmentally compatible manner). A "unitary" absorbent article refers to absorbent articles which are formed as a single structure or as separate parts united together to form a coordinated entity so that they do not require separate manipulative parts such as a separate holder and pad.

A preferred embodiment of a unitary disposable absorbent article made in accordance herewith is the catamenial pad, sanitary napkin 10, shown in FIG. 1. As used herein, the term "sanitary napkin" refers to an absorbent article which is worn by females adjacent to the pudendal region, generally external to the urogenital region, and which is intended to absorb and contain menstrual fluids and other vaginal discharges from the wearer's body (e.g., blood, menses, and urine). Interlabial devices which reside partially within and partially external to the wearer's vestibule are also within the scope of this invention. It should be understood, however, that the present invention is also applicable to other feminine hygiene or catamenial pads, or other absorbent articles such as diapers, incontinent pads, training pants, and the like, as well as other webs designed to facilitate fluid transport away from a surface such as disposable towels, facial tissues, wipes, and the like.

It is to be understood that the overall size, shape, and/or configuration of the absorbent article, if any, into which the webs according to the present invention are incorporated, or utilized in conjunction with, have no criticality or functional relationship to the principles of the present invention. Such parameters, however, must be considered along with the intended fluid and intended functionality when determining appropriate web configurations.

Sanitary napkin 10 is illustrated as having two surfaces, first surface 10a, sometimes referred to as a wearer-contacting or facing surface, a body-contacting or facing surface or "body surface", and second surface 10b (shown in FIG. 2), sometimes referred to as a garment-facing or contacting surface, or "garment surface". The sanitary napkin 10 is shown in FIG. 1 as viewed from its first surface 10a. The first surface 10a is intended to be worn adjacent to the body of the wearer. The second surface 10b of the sanitary napkin 10 (shown in FIG. 2) is on the opposite side and is intended to be placed adjacent to the wearer's undergarment when the sanitary napkin 10 is worn.

Referring to FIG. 1, the sanitary napkin 10 has two centerlines, a longitudinal centerline "L" and a transverse centerline "T". The term "longitudinal", as used herein, refers to a line, axis or direction in the plane of the sanitary napkin 10 that is generally aligned with (e.g., approximately parallel to) a vertical plane which bisects a standing wearer into left and right body halves when the sanitary napkin 10 is worn. The terms "transverse" or "lateral" as used herein, are interchangeable and refer to a line, axis or direction which lies within the plane of the sanitary napkin 10 that it generally perpendicular to the longitudinal direction. FIG. 1 also shows that the sanitary napkin 10 has a periphery 20 which is defined by the outer edges of the sanitary napkin 10 in which the longitudinal edges (or "side edges") are designated 21 and the end edges (or "ends") are designated 22.

FIG. 1 is top plan view of a sanitary napkin 10 of the present invention in a substantially flat state with portions of the sanitary napkin being cut away to more clearly show the construction of the sanitary napkin 10 and with the portion of the sanitary napkin 10 which faces or contacts the wearer 10a oriented towards the viewer. As shown in FIG. 1, the sanitary napkin 10 comprises a liquid pervious topsheet 12 of the present invention, a liquid impervious backsheet 13 joined with the topsheet 12, an absorbent core 14 positioned between the topsheet 12 and the backsheet 13, and a secondary topsheet or acquisition layer 15 positioned between the topsheet 12 and the absorbent core 14.

The sanitary napkin 10 preferably includes optional side flaps or "wings" 24 that are folded around the crotch portion of the wearer's panty. The side flaps 24 can serve a number of purposes, including, but not limited to helping to hold the napkin in proper position while protecting the wearer's panty from soiling and keeping the sanitary napkin secured to the wearer's panty.

Figure 2:
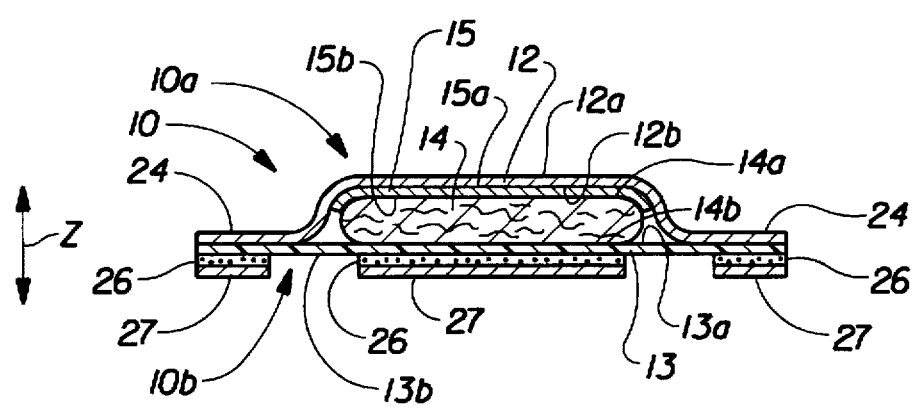
FIG. 2 is a cross-sectional view of the sanitary napkin of FIG. 1 taken along section line 2—2.

FIG. 2 is a cross-sectional view of the sanitary napkin 10 taken along section line 2—2 of FIG. 1. As can be seen in FIG. 2, the sanitary napkin 10 preferably includes an adhesive fastening means 26 for attaching the sanitary napkin 10 to the undergarment of the wearer. Removable release liners 27 cover the adhesive fastening means 26 to keep the adhesive from sticking to a surface other than the crotch portion of the undergarment prior to use.

The topsheet 12 has a first surface 12a and a second surface 12b positioned adjacent to and preferably secured to a first surface 15a of the fluid acquisition layer 15 to promote fluid transport from the topsheet to the acquisition layer. The second surface 15b of the acquisition layer 15 is positioned adjacent to and is preferably secured to the first surface 14a of an absorbent core or fluid storage layer 14 to promote fluid transport from the acquisition layer to the absorbent core. The second surface 14b of the absorbent core 14 is positioned adjacent to and is preferably secured to the first surface 13a of the backsheet 13.

In addition to having a longitudinal direction and a transverse direction, the sanitary napkin 10 also has a "Z" direction or axis, which is the direction proceeding downwardly through the topsheet 12 and into whatever fluid storage layer or core 14 that may be provided. The objective is to provide a substantially continuous path between the topsheet 12 and the underlying layer or layers of the absorbent article herein, such that fluid is drawn in the "Z" direction and away from the topsheet of the article and toward its ultimate storage layer.

The absorbent core 14 may be any absorbent means which is capable of absorbing or retaining liquids (e.g., menses and/or urine). As shown in FIG. 2, the absorbent core 14 has a body surface 14a, a garment facing surface 14b, side edges, and end edges. The absorbent core 14 may be manufactured in a wide variety of sizes and shapes (e.g. rectangular, oval, hourglass, dogbone, asymmetric, etc.) and from a wide variety of liquid-absorbent materials commonly used in sanitary napkins and other absorbent articles such as communitive wood pulp which is generally referred to as airfelt. Examples of other suitable absorbent materials include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combination of materials, or mixtures of these.

The configuration and construction of the absorbent core may also be varied (e.g., the absorbent core may have varying caliper zones (e.g. profiled so as to be thicker in the center), hydrophilic gradients, superabsorbent gradients or lower density or lower average basis weight acquisition zones; or may comprise one or more layers or structures). The total absorbent capacity of the absorbent core, should, however, be compatible with the design loading and the intended use of the absorbent article. Further, the size and absorbent capacity of the absorbent core may be varied to accommodate different uses such as incontinent pads, pantiliners, regular sanitary napkins, or overnight sanitary napkins.

Exemplary absorbent structures for use as the absorbent core in the present invention are described in U.S. Pat. No. 4,950,264 issued to Osborn on Aug. 21, 1990; U.S. Pat. No. 4,610,678 issued to Weisman et al. on Sep. 9, 1986; U.S. Pat. No. 4,834,735 issued to Alemany et al. on May 30, 1989; and European Patent Application No. 0 198 683, the Procter & Gamble Company, published Oct. 22, 1986 in the name Duenk, et al. The disclosure of each of these patents is incorporated herein by reference.

The backsheet 13 and the topsheet 12 are positioned adjacent the garment facing surface and the body facing surface respectively of the absorbent core 14 and are preferably joined thereto and to each other by attachment means (not shown) such as those well known in the art. For example, the backsheet 13 and/or the topsheet 12 may be secured to the absorbent core or to each other by a uniform continuous layer of adhesive, a patterned layer of adhesive or any array of separate lines, spirals or spots of adhesive. Adhesives which have been found to be satisfactory are manufactured by H. B. Fuller Company of St. Paul, Minn. under the designation HL-1258, and by Findlay of Minneapolis, Minn., under the designation H-2031. The attachment means will preferably comprise an open pattern network of filaments of adhesive as disclosed in U.S. Pat. No. 4,573,986 issued to Minetola et al. on Mar. 4, 1986, the disclosure of which is incorporated herein by reference. An exemplary attachment means of an open patterned network of filaments comprises several lines of adhesive filaments swirled into a spiral pattern such as illustrated by the apparatus and method shown in U.S. Pat. No. 3,911,173 issued to Sprague, Jr. on Oct. 7, 1975; U.S. Pat. No. 4,785,996 issued to Zieker, et al. on Nov. 22, 1978 and U.S. Pat. No. 4,842,666 issued to Werenicz on Jun. 27, 1989. The disclosures of each of these patents are incorporated herein by reference. Alternatively, the attachment means may comprise heat bonds, pressure bonds, ultrasonic bonds, dynamic mechanical bonds or any other suitable attachment means or combinations of these attachment means as are known in the art.

The backsheet 13 is impervious to liquids (eg., menses and/or urine) and is preferably manufactured from a thin plastic film, although other flexible liquid impervious materials may also be used. As used herein, the term "flexible" refers to materials which are compliant and are more readily conformed to the general shape and contours of the human body. The backsheet 13 prevents the exudates absorbed and contained in the absorbent core from wetting articles which contact the sanitary napkin 10 such as pants, pajamas and undergarments. The backsheet 13 may thus comprise a woven or nonwoven material, polymeric films such as thermoplastic films of polyethylene or polypropylene, or composite materials such as a film-coated nonwoven material. Preferably, the backsheet of the polyethylene film having a thickness of from about 0.012 mm (0.5 mil) to about 0.051 mm (2.0 mil). Exemplary polyethylene films are manufactured by Clopay Corporation of Cincinnati, Ohio, under the designation P18-1401 and by Tredegar Film Products of Terre Haute, Ind., under the designation XP-9818. The backsheet is preferably embossed and/or matte finished to provide a more clothlike appearance. Further, the backsheet 13 may permit vapors to escape from the absorbent core 14 (i.e., breathable) while still preventing exudates from passing through the backsheet 13.

In use, the sanitary napkin 10 can be held in place by any support means or attachment means (not shown) well-known for such purposes. Preferably, the sanitary napkin is placed in the user's undergarment or panty and secured thereto by a fastener such as an adhesive. The adhesive provides a means for securing the sanitary napkin in the crotch portion of the panty. Thus, a portion or all of the outer or garment facing surface 13b of the backsheet 13 is coated with adhesive. Any adhesive or glue used in the art for such purposes can be used for the adhesive herein, with pressure-sensitive adhesives being preferred. Suitable adhesives are manufactured by H. B. Fuller Company of St. Paul, Minn., under the designation 2238. Suitable adhesive fasteners are also described in U.S. Pat. No. 4,917,697. Before the sanitary napkin is placed in use, the pressure-sensitive adhesive is typically covered with a removable release liner 27 in order to keep the adhesive from drying out or adhering to a surface other than the crotch portion of the panty prior to use. Suitable release liners are also described in the above-referenced U.S. Pat. No. 4,917,697. Any commercially available release liners commonly used for such purposes can be utilized herein. A non-limiting example of a suitable release liner is BL30MG-A Silox 4P/0, which is manufactured by the Akrosil Corporation of Menasha, Wis. The sanitary napkin 10 of the present invention is used by removing the release liner and thereafter placing the sanitary napkin in a panty so that the adhesive contacts the panty. The adhesive maintains the sanitary napkin in its position within the panty during use.

In a preferred embodiment of the present invention, the sanitary napkin has two flaps 24 each of which are adjacent to and extend laterally from the side edge of the absorbent core. The flaps 24 are configured to drape over the edges of the wearer's panties in the crotch region so that the flaps are disposed between the edges of the wearer's panties and the thighs. The flaps serve at least two purposes. First, the flaps help serve to prevent soiling of the wearer's body and panties by menstrual fluid, preferably by forming a double wall barrier along the edges of the panty. Second, the flaps are preferably provided with attachment means on their garment surface so that the flaps can be folded back under the panty and attached to the garment facing side of the panty. In this way, the flaps serve to keep the sanitary napkin properly positioned in the panty. The flaps can be constructed of various materials including materials similar to the topsheet, backsheet, tissue, or combination of these materials. Further, the flaps may be a separate element attached to the main body of the napkin or can comprise extensions of the topsheet and backsheet (i.e., unitary). A number of sanitary napkins having flaps suitable or adaptable for use with the sanitary napkins of the present invention are disclosed in U.S. Pat. No. 4,687,478 entitled "Shaped Sanitary Napkin With Flaps", which issued to Van Tilburg on Aug. 18, 1987; and U.S. Pat. No. 4,589,876 entitled "Sanitary Napkin", which issued to Van Tilburg on May 20, 1986. The disclosure of each of these patents is hereby incorporated herein by reference.

In a preferred embodiment of the present invention, an acquisition layer(s) 15 may be positioned between the topsheet 12 and the absorbent core 14. The acquisition layer 15 may serve several functions including improving wicking of exudates over and into the absorbent core. There are several reasons why the improved wicking of exudates is important, including providing a more even distribution of the exudates throughout the absorbent core and allowing the sanitary napkin 10 to be made relatively thin. The wicking referred to herein may encompass the transportation of liquids in one, two or all directions (i.e., in the x-y plane and/or in the z-direction). The acquisition layer may be comprised of several different materials including nonwoven or woven webs of synthetic fibers including polyester, polypropylene, or polyethylene; natural fibers including cotton or cellulose; blends of such fibers; or any equivalent materials or combinations of materials. Examples of sanitary napkins having an acquisition layer and a topsheet are more fully described in U.S. Pat. No. 4,950,264 issued to Osborn and U.S. patent application Ser. No. 07/810,774, "Absorbent Article Having Fused Layers", fired Dec. 17, 1991 in the names of Cree, et al. The disclosures of each of these references are hereby incorporated herein by reference. In a preferred embodiment, the acquisition layer may be joined with the topsheet by any of the conventional means for joining webs together, most preferably by fusion bonds as is more fully described in the above-referenced Cree application.

Catamenial pads may be constructed as follows. Onto silicone-coated release paper a spiral pattern of H2031 Findlay hot melt adhesive is applied at 0.04 g per in². This adhesive layer is transferred onto the top (wearer-facing) side of a secondary topsheet by rolling the secondary topsheet and coated release paper together with a hand roller. The secondary topsheet is formed of a nonwoven material known as Fort Howard Airlaid Tissue, Grade 817, commercially available from the Fort Howard Corp. of Green Bay, Wis. A topsheet of the present invention is applied to the adhesive side of the secondary topsheet and the two are bonded by gently pressing them together with a hand roller. Two strips of one-quarter-inch double-sided tape are applied along both long edges of a polyethylene backsheet. The absorbent core is added to construct the complete absorbent structure.

Figure 3:
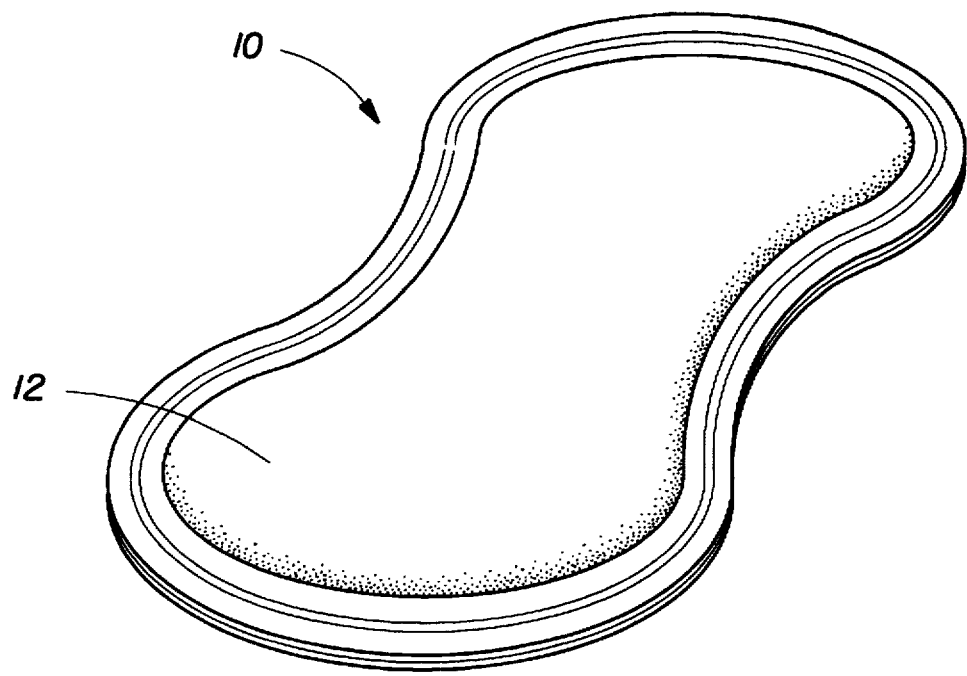
FIG. 3 is an enlarged, perspective illustration of a representative absorbent article in the form of a sanitary napkin or catamenial pad made in accordance with the present invention.

To construct a representative absorbent article according to the embodiment of FIG. 3, the following materials are utilized for the components of the absorbent structure. The absorbent article of FIG. 3 (catamenial pad) is structurally similar to that of FIGS. 1 and 2, except that it exhibits an hourglass-shaped overall profile. The core layer is assembled as follows: A sheet of the same Fort Howard material as the secondary topsheet is cut to a finished size of 190 mm by 143 mm. A silicone-coated release paper containing a spiral pattern of H2031 Findlay hot melt adhesive is applied to the Fort Howard at 0.04 grams per square inch. The silicone-coated release paper which is used to transfer the glue is left on the Fort Howard and a 190 mm by 65 mm template is placed onto the middle of the sheet with the lengthwise ends aligned with the lengthwise ends of the Fort Howard. The Fort Howard is then folded over the template to crease the material, dividing the material into three portions. The template is then removed, leaving the glue on the creased Fort Howard. Particulate absorbent gelling material in the form of Nalco 1180 AGM is then evenly distributed in the amount of 0.68 grams per pad onto the glue side of the Fort Howard, nonwoven material. Next, 190 mm of quarter inch double-sided tape is applied to the inside edge of the Fort Howard, which is then folded over by the creases so that the taped edge is on top. The resulting storage core has a finished dimension of 190 mm by 65 mm. The secondary topsheet is adhesively bonded to the topsheet. The storage/core layer is adhesively bonded to the polyethylene backsheet by two strips of quarter inch double-sided tape.

The topsheet and absorbent structure assembly are then combined. Nex, a sheet of Teflon ® is placed over the assembled structure. The edges of the product are sealed with an appropriately shaped die, attached to an iron and heated to a temperature above the melting point of the polyethylene topsheet and backsheet. The iron die is applied to the material with hand pressure to seal the edges. The catamenial pad is then cut from the excess material using a pair of hand scissors.

Figure 4:
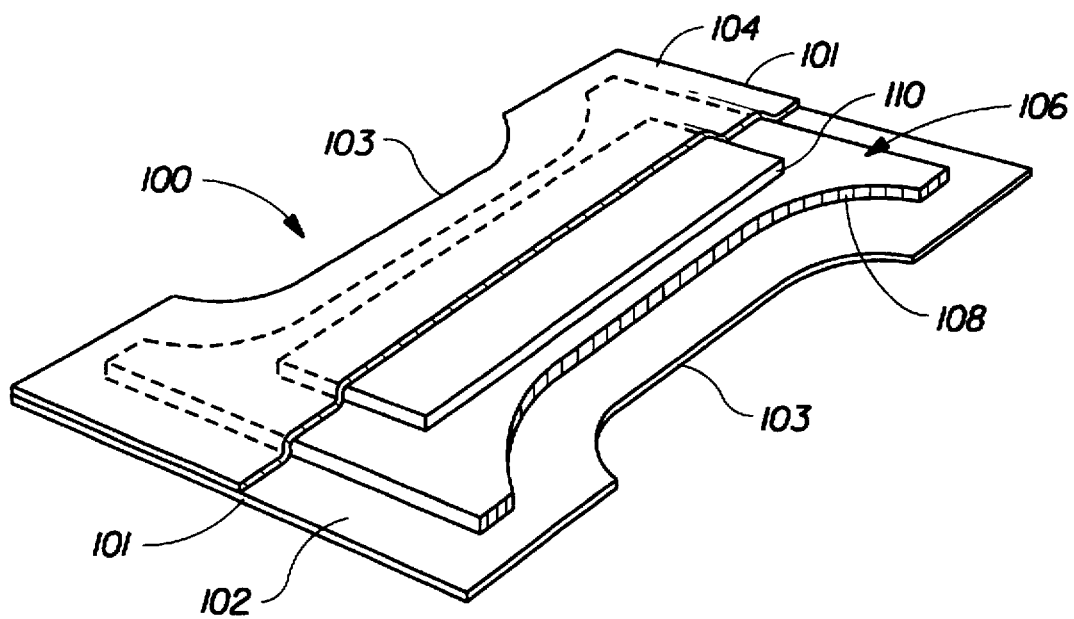
FIG. 4 is an enlarged, partially segmented, perspective illustration of a representative absorbent article in the form of a diaper made in accordance with the present invention.

A representative embodiment of a disposable absorbent article in the form of a diaper 100, is shown in FIG. 4. As used herein, the term "diaper" refers to a garment generally worn by infants and incontinent persons that is worn about the lower torso of the wearer. It should be understood, however, that the present invention is also applicable to other absorbent articles such as incontinent briefs, incontinent pads, training pants, diaper inserts, sanitary napkins, facial tissues, paper towels, and the like. The diaper 100 depicted in FIG. 4 is a simplified absorbent article that could represent a diaper prior to its being placed on a wearer. It should be understood, however, that the present invention is not limited to the particular type or configuration of diaper shown in FIG. 4.

FIG. 4 is a perspective view of the diaper 100 in its uncontracted state (i.e., with all the elastic induced contraction removed) with portions of the structure being cut-away to more clearly show the construction of the diaper 100. The portion of the diaper 100 which contacts the wearer faces the viewer. The diaper 100 is shown in FIG. 4 to comprise a liquid pervious topsheet 104 of the present invention; a liquid impervious backsheet 102 joined with the topsheet 104; and an absorbent core 106 positioned between the topsheet 104 and the backsheet 102. Additional structural features such as elastic members and fastening means for securing the diaper in place upon a wearer (such as tape tab fasteners) may also be included.

While the topsheet 104, the backsheet 102, and the absorbent core 106 can be assembled in a variety of well known configurations, a preferred diaper configuration is described generally in U.S. Pat. No. 3,860,003 (Buell), issued Jan. 14, 1975, the disclosure of which is incorporated by reference. Alternatively preferred configurations for disposable diapers herein are also disclosed in U.S. Pat. No. 4,808,178 (Aziz et al), issued Feb. 28, 1989; U.S. Pat. No. 4,695,278 (Lawson), issued Sep. 22, 1987; and U.S. Pat. No. 4,816,025 Foreman), issued Mar. 28, 1989, the disclosures of each of these patents hereby being incorporated herein by reference.

FIG. 4 shows a preferred embodiment of the diaper 100 in which the topsheet 104 and the backsheet 102 are co-extensive and have length and width dimensions generally larger than those of the absorbent core 106. The topsheet 104 is joined with and superimposed on the backsheet 102 thereby forming the periphery of the diaper 100. The periphery defines the outer perimeter or the edges of the diaper 100. The periphery comprises the end edges 101 and the longitudinal edges 103.

As indicated, the topsheet 104 of the present invention is preferably compliant, soft feeling, and non-irritating to the wearer's skin.

The backsheet 102 is impervious to liquids and is preferably manufactured from a thin plastic film, although other flexible liquid impervious materials may also be used. The backsheet 102 prevents the exudates absorbed and contained in the absorbent core 106 from wetting articles which contact the diaper 100 such as bed sheets and undergarments. Preferably, the backsheet 102 is polyethylene film having a thickness from about 0.012 mm (0.5 mil) to about 0.051 centimeters (2.0 mils), although other flexible, liquid impervious materials can be used. As used herein, the term "flexible" refers to materials which are is compliant and which will readily conform to the general shape and contours of the wearer's body.

A suitable polyethylene film is manufactured by Monsanto Chemical Corporation and marketed in the trade as Film No. 8020. The backsheet 102 is preferably embossed and/or matte finished to provide a more clothlike appearance. Further, the backsheet 102 may permit vapors to escape from the absorbent core 106 while still preventing exudates from passing through the backsheet 102.

The size of the backsheet 102 is dictated by the size of the absorbent core 106 and the exact diaper design selected. In a preferred embodiment, the backsheet 102 has a modified hourglass-shape extending beyond the absorbent core 106 a minimum distance of at least about 1.3 centimeters to about 2.5 centimeters (about 0.5 to about 1.0 inch) around the entire diaper periphery.

The topsheet 104 and the backsheet 102 are joined together in any suitable manner. As used herein, the term "joined" encompasses configurations whereby the topsheet 104 is directly joined to the backsheet 102 by affixing the topsheet 104 directly to the backsheet 102, and configurations whereby the topsheet 104 is indirectly joined to the backsheet 102 by affixing the topsheet 104 to intermediate members which in turn are affixed to the backsheet 102. In a preferred embodiment, the topsheet 104 and the backsheet 102 are affixed directly to each other in the diaper periphery by attachment means (not shown) such as an adhesive or any other attachment means as known in the art. For example, a uniform continuous layer of adhesive, a patterned layer of adhesive, or an array of separate lines or spots of adhesive can be used to affix the topsheet 104 to the backsheet 102.

Tape tab fasteners (not shown for clarity) are typically applied to the back waistband region of the diaper 102 to provide a fastening means for holding the diaper on the wearer. The tape tab fasteners can be any of those well known in the art, such as the fastening tape disclosed in U.S. Pat. No. 3,848,594 (Buell), issued Nov. 19, 1974, the disclosure of which is hereby incorporated by reference. These tape tab fasteners or other diaper fastening means are typically applied near the corners of the diaper 100.

Elastic members (also not shown for clarity) are disposed adjacent the periphery of the diaper 100, preferably along each longitudinal edge 103, so that the elastic members tend to draw and hold the diaper 100 against the legs of the wearer. Alternatively, the elastic members can be disposed adjacent either or both of the end edges 101 of the diaper 100 to provide a waistband as well as or rather than leg cuffs. For example, a suitable waistband is disclosed in U.S. Pat. No. 4,515,595 (Kievit et al), issued May 7, 1985, the disclosure of which is hereby incorporated by reference. In addition, a method and apparatus suitable for manufacturing a disposable diaper having elastically contractible elastic members is described in U.S. Pat. No. 4,081,301 (Buell), issued Mar. 28, 1978, the disclosure of which is hereby incorporated herein by reference.

The elastic members are secured to the diaper 100 in an elastically contractible condition so that in a normally unrestrained configuration, the elastic members effectively contract or gather the diaper 100. The elastic members can be secured in an elastically contractible condition in at least two ways. For example, the elastic members can be stretched and secured while the diaper 100 is in an uncontracted condition. Alternatively, the diaper 100 can be contracted, for example, by pleating, and the elastic members secured and connected to the diaper 100 while the elastic members are in their unrelaxed or unstretched condition. The elastic members may extend along a portion of the length of the diaper 100. Alternatively, the elastic members can extend the entire length of the diaper 100, or any other length suitable to provide an elastically contractible line. The length of the elastic members is dictated by the diaper design.

The elastic members can be in a multitude of configurations. For example, the width of the elastic members can be varied from about 0.25 millimeters (0.01 inches) to about 25 millimeters (1.0 inch) or more; the elastic members can comprise a single strand of elastic material or can comprise several parallel or non-parallel strands of elastic material; or the elastic members can be rectangular or curvilinear. Still further, the elastic members can be affixed to the diaper in any of several ways which are known in the art. For example, the elastic members can be ultrasonically bonded, heat and pressure sealed into the diaper 100 using a variety of bonding patterns or the elastic members can simply be glued to the diaper 100.

The absorbent core 106 of the diaper 100 is positioned between the topsheet 104 and the backsheet 102. The absorbent core 106 can be manufactured in a wide variety of sizes and shapes (e.g., rectangular, hourglass, asymmetrical, etc.). The total absorbent capacity of the absorbent core 106 should, however, be compatible with the design liquid loading for the intended use of the absorbent article or diaper. Further, the size and absorbent capacity of the absorbent core 106 can vary to accommodate wearers ranging from infants through adults.

As shown in FIG. 4, the absorbent core 106 includes a fluid distribution member 108. In a preferred configuration such as depicted in FIG. 4, the absorbent core 106 preferably further includes an acquisition layer or member 110 in fluid communication with the fluid distribution member 108 and located between the fluid distribution member 108 and the topsheet 104. The acquisition layer or member 110 may be comprised of several different materials including nonwoven or woven webs of synthetic fibers including polyester, polypropylene, or polyethylene, natural fibers including cotton or cellulose, blends of such fibers, or any equivalent materials or combinations of materials.

In use, the diaper 100 is applied to a wearer by positioning the back waistband region under the wearer's back, and drawing the reminder of the diaper 100 between the wearer's legs so that the front waistband region is positioned across the front of the wearer. The tape-tab or other fasteners are then secured preferably to outwardly facing areas of the diaper 100.

VI. Test Method—Measuring Contact Angle

A. Unapertured Films

The contact angle formed between the solid surface of an unapertured film and the meniscus of a water drop is a measure of solid substrate hydrophilicity/hydrophobicity. The lower the water contact angle, the higher the substrate hydrophilicity. The method described below for determining contact angle, and more specifically the time at which the contact angle for a given polymer/surfactant mixture to be processed is at least about 30°, allows the determination of when a flat, unapertured film must be subjected to the first aperturing process in accordance with the present invention.

A model NRL Goniometer (Rame-Hart, Inc., Mountain Lake, N.J.) may be used to measure contact angle. A 4 µL droplet of deionized water is placed on a flat film (i.e., unapertured) sample sitting on the goniometer platform to measure contact angle at room temperature.

The goniometer is calibrated first using a bubble level to ensure that the sample platform is level. The instrument light is adjusted such that the droplet is clearly visible. A 4 µL droplet of deionized water is placed on a ⅜ in. thick piece of Lexan® (available from General Electric) which has been previously washed with methanol and allowed to dry completely. The contact angle of the drop is measured. The instrument is properly calibrated if the contact angle of water on Lexan fills within the range of 68+/−3 degrees.

Sample measurements are obtained according to the following procedure:

1) A representative sample is cut from an unapertured web, the sample having dimensions of approximately 2.5 cm×5 cm.
2) The sample is placed on the sample platform. Adhesive tape is used, if necessary, to secure the sample on the platform and keep the sample flat.
3) A 4 µL droplet of deionized water is placed onto the sample.
4) The position of the platform is adjusted (vertically and horizontally) and focused to get a clear view of the droplet.
5) The contact angle is measured and recorded after the water droplet has been on the sample for at least 2 minutes, to ensure equilibration of the sample.
6) Steps 1–5 are repeated 3 times for each sample tested.
7) The average contact angle for each sample is calculated.

Contact angle measurements are obtained for a given unapertured film after extrusion at different times until it is determined when the web has a contact angle for water of at least about, e.g., 30°. This will define the time at which aperture formation of the unapertured film must have occurred to minimize surfactant wash-off.

B. Previously Apertured Films
i. Apertures Formed in Opposite Directions

In those embodiments where a second phase of aperture formation is to be conducted in the direction opposite the first phase of aperture formation, the time determined according to Section VI-A for the flat film will apply to the previously apertured film. That is, where aperture formation will occur in opposite directions, both phases of aperture formation must occur within the time after polymer/surfactant extrusion determined for the flat film. This is explained by the fact that during formation of apertures in the first phase, the male side (i.e., the side contacting the forming structure) of that apertured web will be exposed to essentially no fluid pressure during aperture formation in the second phase (though there may be minimal wash-off from, e.g., indirect fluid contact). As such, relatively few of the surfactant molecules that have bloomed to the web's surface (male side) before aperturing of the flat film will be washed off. Thus, the male side of the web apertured in the first phase, which will be exposed to fluid pressures in the second phase, will have a contact angle, at any given time, essentially equal to an unapertured web.

By way of illustration, if it is determined in Section VI-A that a given continuous polymer/surfactant web must be apertured within, e.g., five (5) hours after film extrusion to ensure that the contact angle is not less than about 30°, and apertures will be formed in opposite directions, then both phases of aperture formation must be conducted within five (5) hours of film extrusion.

ii. Apertures Formed in the Same Direction

In those embodiments where a second phase of aperture formation is to be conducted in the same direction as the first phase of aperture formation, the following procedure is utilize for determining when each phase of aperture formation must occur to minimize wash off.

For purposes of determining contact angle (and corresponding aperturing times for the second aperturing phase), the unapertured film is processed on a forming structure having desired aperture patterns, as well as regions having no apertures. The entire surface of the unapertured film is exposed to fluid jets, resulting in an apertured web having aperture patterns similar to the forming structure, as well as unapertured regions. Because the unapertured regions are exposed to the fluid pressures in the first forming structure, the contact angle of the surface measured in these regions will be essentially the same as the contact angle of the apertured surface that will be subjected to water pressures during the second phase of aperture formation.

The procedure described in Section VI-A above is used to determine contact angle of the apertured film, except that the sample used in step 1) is a 1 in.×2 in. sample cut from an unapertured region of the web. Also, in step 2), the sample is placed on the sample platform such that the 4 µl droplet of deionized water is placed on the surface that was exposed to the water jets in the first phase of aperture formation.

It is believed that the description contained herein will enable one skilled in the art to practice the present invention in many and varied forms. Nonetheless, the following exemplary embodiments are set forth for purposes of illustration:

EXAMPLE 1

Formation of a Durably Wettable Polymeric Web Having Micro- and Macro-sized Apertures Formed in Opposite Directions A resin mixture comprising low density polyethylene and surfactant (Atmer 100®), available from Tredegar Film Products (Richmond, Va.) as X-15565 are fed to an extruder. This resin mixture provides an extruded film comprising approximately 1% surfactant, by total weight of the film. The extruder is a 24:1 length:diameter single screw extruder with conventional polyethylene mixing screw (available from Egan Machinery, N.J.). A homogeneous melt is delivered to a 44 in. wide flexible lip cast die. Temperature in the die zone is set to 480° F. A flat film having a thickness of about 25 μm is pinned to chill rolls at a line speed of about 200 feet per minute. While passing the treater, corona discharge treatment (180 volt) is optionally applied to the surface of the film in which the macro-sized holes will originate. After the edge of the film is removed by a trimmer, the film is slit and wound up into roll form.

A sample of the unapertured film is cut from the finishing roll. Contact angle measurements are conducted on the film according to the Test Method (Section VI-A) description to determine when aperture formation must be conducted. It is determined that for this film, aperture formation of the unapertured web must be conducted within 14 hours of film formation (i.e., extrusion). Per the description in Section VI-B, because the second phase of aperture formation is conducted in a direction opposite that of the first phase, the second phase must also be performed within 14 hours of film extrusion.

The extruded flat film comprising polyethylene and surfactant is fed onto a forming screen at a speed of 200 feet per minute and is subjected to the high pressure jet. The screen used is 80 mesh, to provide a microapertured web. The water temperature is 175° F. and the pressure is 550 psi. The micro-apertured film is then wound onto a take up roll.

The apertured film is reverse-wrapped on a second forming screen at a speed of 150 feet per minute and is subjected to the high pressure jet. As indicated above, this aperturing phase of the process is conducted at a time not greater than 14 hours after film extrusion. The screen used is 56/4 circular macroaperture pattern, where hole diameter is 56 mils and the distance between holes is 4 mils. The water temperature is 145° F. and the pressure is 525 psi. The apertured film is dried, corona discharge treated, then trimmed and slit to 8 in. wide and wound onto two take up rolls.

EXAMPLE 2

Formation of a Durably Wettable Polymeric Web Having Micro- and Macro-sized Apertures Formed in Opposite Directions A resin mixture comprising low density polyethylene and surfactant (Atmer 100®), available from Tredegar Film Products (Richmond, Va.) as X-15663 are fed to an extruder. This resin mixture provides an extruded film comprising approximately 2% surfactant, by total weight of the film. The extruder is a 24:1 length:diameter single screw extruder with conventional polyethylene mixing screw. A homogeneous melt is delivered to a 44 in. wide flexible lip cast die. Temperature in the F die zone is set to 480° F. A flat film 25 μm thick is pinned to chill rolls at a line speed of about 200 feet per minute. While passing the treater, corona discharge treatment (180 volt) is optionally applied to the surface of the film within which the macro-sized apertures will originate. After the edge of the film is removed by a trimmer, the film is slit and wound up into roll form.

A sample of film is cut from the finishing roll. Contact angle measurements are conducted on the film according to the Test Method (Section VI-A) description to determine when aperture formation must be conducted. It is determined that for this film aperture formation of the unapertured web must be conducted within 6 hours of film formation (i.e., extrusion). In accordance with the description in Section VI-B above, because the second phase of aperture formation is conducted in a direction opposite that of the first phase, the second phase must also be performed not greater than 6 hours after film extrusion.

The extruded flat film comprising polyethylene and surfactant is fed onto a forming screen at a speed of 200 feet per minute and is subjected to the high pressure jet. The screen used is 80 mesh, to provide a microapertured web. The water temperature is 175° F. and the pressure is 550 psi. The micro-apertured film is then wound onto a take up roll.

The apertured film is reverse-wrapped on a second forming screen at a speed of 150 feet per minute and also subjected to the high pressure jet. As indicated above, this aperturing phase of the process is conducted at a time not greater than 6 hours after film extrusion. The screen used is 56/4 circular macroaperture pattern, where hole diameter is 56 mils and the distance between holes is 4 mils. The water temperature is 145° F. and the pressure is 525 psi. The apertured film is dried, corona discharge treated, then trimmed and slit to 8 in. wide and wound onto two take up rolls.

As is demonstrated by a comparison of Examples 1 and 2, the resin/surfactant blend containing 2% surfactant dictates that aperture formation occur much sooner than the blend with 1% surfactant mixture, in order to minimize surfactant wash-off in accordance with the present invention.

What is claimed is:

1. A process for forming a single-layer, durably wettable apertured polymeric web, the process comprising the steps of:

(a) melting a mixture of at least one thermoplastic polymer and at least one migratable surfactant and extruding the mixture to form a substantially continuous polymeric film;

(b) continuously supporting the film on a forming structure exhibiting a multiplicity of apertures which place the opposed surface of the forming structure in fluid communication with one another, the forming structure moving in a direction parallel to the direction of travel of the film and carrying the film in the direction; and (c) applying a fluid pressure differential across the thickness of the film along the direction of movement of the forming structure exhibiting the apertures, the fluid pressure differential being sufficiently great to cause the film to rupture in those areas coinciding with the apertures in the forming structure;

wherein aperture formation in Step (c) is performed when the surface of the substantially continuous film formed in Step (a) has a contact angle for water of at least about 30°.

2. The process of claim 1 wherein the film is urged into substantial compliance with the forming structure exhibiting a multiplicity of apertures by subjecting the non-film contacting surface of the forming structure to vacuum.

3. The process of claim 1 wherein an apertured mask element is interposed between the fluid pressure differential and the film to limit the portions of the film to be subjected to the fluid pressure differential to those areas coinciding with the apertures in the mask element.

4. The process of claim 1 wherein the thermoplastic polymer is a polyolefin.

5. The process of claim 1 wherein the thermoplastic polymer is selected from the group consisting of polyethylene, polypropylene, and mixtures thereof.

6. The process of claim 1 wherein the migratable surfactant is selected from the group consisting of sorbitan esters, silicone copolymers, fluorochemicals, and mixtures thereof.

7. The process of claim 6 wherein the migratable surfactant is a sorbitan ester.

8. The process of claim 1 wherein the migratable surfactant comprises up to about 10%, by weight, of the thermoplastic polymer/migratable surfactant mixture.

9. The process of claim 8 wherein the migratable surfactant comprises up to about 5%, by weight, of the thermoplastic polymer/migratable surfactant mixture.

10. The process of claim 1 wherein the apertures of the forming structure are macroscopic in size.

11. The process of claim 1 wherein the apertures of the forming structure are microscopic in size.

12. The process of claim 1 wherein the substantially continuous polymeric film formed in step (a) is subjected to corona discharge treatment before performing step (b).

13. The process of claim 1 wherein the apertured web formed in step (c) is thereafter subjected to corona discharge treatment.

14. A multi-phase process for forming a single-layer, durably wettable apertured polymeric web, the process comprising the steps of:

(a) melting a mixture of at least one thermoplastic polymer and at least one migratable surfactant and extruding the mixture to form a substantially continuous polymeric film;

(b) continuously supporting the film on a first forming structure exhibiting a multiplicity of apertures which place the opposed surfaces of the forming structure in fluid communication with one another, the forming structure moving in a direction parallel to the direction of travel of the film and carrying the film in the direction;

(c) applying a first fluid pressure differential across the thickness of the film along the direction of movement of the forming structure exhibiting the apertures, the fluid pressure differential being sufficiently great to cause the film to rupture in those areas coinciding with the apertures in the forming structure;

(d) continuously supporting the apertured web on a second forming structure exhibiting a multiplicity of apertures which place the opposed surfaces of the second forming structure in fluid communication with one another, the second forming structure moving in a direction parallel to the direction of travel of the apertured web and carrying the apertured web in the direction; and (e) applying a second fluid pressure differential across the thickness of the apertured web along the direction of movement of the forming structure, wherein the second fluid pressure differential is sufficiently great to rupture the apertured web in those areas coinciding with the apertures in the second forming structure, while substantially maintaining the integrity of the apertures formed by the first fluid pressure differential;

wherein aperture formation in Step (c) is performed when the film formed in Step (a) has a contact angle for water of at least about 30°, and wherein aperture formation in Step (e) is performed when the surface of the apertured web formed in Step (c) that will be subjected to the second fluid pressure differential in the second forming structure has a contact angle for water of at least about 30°.

15. The process of claim 14 wherein one of the forming structures exhibits a multiplicity of microscopic apertures and the other forming structure exhibits a multiplicity of macroscopic apertures.

16. The process of claim 15 wherein the first forming structure exhibits a multiplicity of microscopic apertures and the second forming structure exhibits a multiplicity of macroscopic apertures.

17. The process of claim 16 wherein microscopic aperturing of the web is carried out across the surface of the web on the first forming structure, the micro-apertured web being thereafter fed from the first forming structure onto the second forming structure, where it is macroscopically apertured.

18. The process of claim 16 wherein the micro-apertured web formed on the first forming structure is fed onto the second forming structure so that the surface of the web which contacted the first forming structure does not contact the second forming structure.

19. The process of claim 16 wherein the micro-apertured web formed on the first forming structure is fed onto the second forming structure so that the surface of the web which contacted the first forming structure contacts the second forming structure.

20. The process of claim 14 wherein both of the forming structures exhibit a multiplicity of microscopic apertures, and wherein the micro-apertured web formed on the first forming structure is fed onto the second forming structure so that the surface of the web which contacted the first forming structure does not contact the second forming structure.

21. The process of claim 14 wherein the film is urged into substantial compliance with the forming structure exhibiting a multiplicity of apertures by subjecting the non-web contacting surface of the forming structure to vacuum.

22. The process of claim 14 wherein only a predetermined portion of the film is caused to rupture in those areas coinciding with the microscopic apertures.

23. The process of claim 14 wherein an apertured mask element is interposed between the fluid pressure differential and the web to limit the portions of the web to be subjected to the fluid pressure differential to those areas coinciding with the apertures in the mask element.

24. The process of claim 14 wherein the micro-apertures imparted to the web and the macro-apertures imparted to the web are maintained in register with one another by avoiding stretching of the web as it is transferred from the first forming structure to the second forming structure.

25. The process of claim 14 wherein the polymeric web is subjected to corona discharge treatment either before step (b), before step (d), or after step (e).

* * * * *

UNITED STATES PATENT AND TRADEMARK OFFICE
CERTIFICATE OF CORRECTION

PATENT NO. : 5,792,412
DATED : August 11, 1998
INVENTOR(S) : Lee et al.

It is certified that error appears in the above-identified patent and that said Letters Patent is hereby corrected as shown below:

Title page,
In the title, delete "MARKING" and insert therefore -- MAKING --.

Column 2,
Line 55, delete "Zinunerli" and insert therefore -- Zimmerli --.

Column 3,
Line 54, delete "at" and insert therefore -- art --.

Column 4,
Line 19, delete "TEE" and inser therefore -- THE --.

Column 6,
Line 22, delete "microsized" and insert therefore -- micro-sized --.
Line 54, between "three" and "dimensional" insert therefore -- - -- (a hyphen).

Column 9,
Line 23, delete "diethanolanine" and insert therefore -- diethanolamine --.
Line 29, after "100" and "645" delete "°" and insert therefore -- ® --.

Column 10,
Line 12, after "Wettable" delete "." (the period) and insert therefore -- , -- (a comma).
Line 22, delete "surf cat" and insert therefore -- surfactant --.

Column 15,
Line 32, delete "Osbom" and insert therefore -- Osborn --.

UNITED STATES PATENT AND TRADEMARK OFFICE
CERTIFICATE OF CORRECTION

PATENT NO. : 5,792,412
DATED : August 11, 1998
INVENTOR(S) : Lee et al.

It is certified that error appears in the above-identified patent and that said Letters Patent is hereby corrected as shown below:

<u>Column 16,</u>
Line 55, between "the" and "sanitary" delete "-" (the hyphen).

Signed and Sealed this

Nineteenth Day of March, 2002

Attest:

JAMES E. ROGAN
Attesting Officer      Director of the United States Patent and Trademark Office